(12) United States Patent
Grover et al.

(10) Patent No.: US 10,449,306 B2
(45) Date of Patent: Oct. 22, 2019

(54) SYSTEMS FOR FLUID DELIVERY WITH WICKING MEMBRANE

(71) Applicant: MEDTRONIC MINIMED, INC., Northridge, CA (US)

(72) Inventors: Benjamin A. Grover, Granada Hills, CA (US); Sherif M. Ali, Porter Ranch, CA (US)

(73) Assignee: Medtronics MiniMed, Inc., Northridge, CA (US)

( * ) Notice: Subject to any disclaimer, the term of this patent is extended or adjusted under 35 U.S.C. 154(b) by 510 days.

(21) Appl. No.: 14/952,068

(22) Filed: Nov. 25, 2015

(65) Prior Publication Data
US 2017/0143914 A1 May 25, 2017

(51) Int. Cl.
*A61M 5/38* (2006.01)
*A61M 5/145* (2006.01)
*A61M 5/142* (2006.01)

(52) U.S. Cl.
CPC ............ *A61M 5/38* (2013.01); *A61M 5/145* (2013.01); *A61M 5/14244* (2013.01); *A61M 5/14566* (2013.01); *A61M 2205/126* (2013.01); *A61M 2205/7527* (2013.01); *A61M 2205/8206* (2013.01)

(58) Field of Classification Search
CPC ............ A61M 5/14244; A61M 5/145; A61M 5/14566; A61M 5/38; A61M 2205/7527; A61M 2205/126; A61M 2205/8206
See application file for complete search history.

(56) References Cited

U.S. PATENT DOCUMENTS

| 3,631,847 | A | 1/1972 | Hobbs, II |
| 4,212,738 | A | 7/1980 | Henne |
| 4,270,532 | A | 6/1981 | Franetzki et al. |
| 4,282,872 | A | 8/1981 | Franetzki et al. |
| 4,373,527 | A | 2/1983 | Fischell |
| 4,395,259 | A | 7/1983 | Prestele et al. |
| 4,433,072 | A | 2/1984 | Pusineri et al. |
| 4,443,218 | A | 4/1984 | Decant, Jr. et al. |
| 4,494,950 | A | 1/1985 | Fischell |
| 4,542,532 | A | 9/1985 | McQuilkin |
| 4,550,731 | A | 11/1985 | Batina et al. |
| 4,559,037 | A | 12/1985 | Franetzki et al. |
| 4,562,751 | A | 1/1986 | Nason et al. |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Jenna Zhang
(74) *Attorney, Agent, or Firm* — Lorenz & Kopf, LLP

(57) ABSTRACT

A fluid reservoir system is provided. The fluid reservoir system includes a fluid reservoir that defines a chamber to receive a fluid, and the fluid reservoir includes an outlet. The fluid reservoir system includes a source of pressure to draw the fluid into the outlet and a wicking membrane is coupled to the fluid reservoir that covers the outlet.

7 Claims, 8 Drawing Sheets

(56) References Cited

U.S. PATENT DOCUMENTS

| | | |
|---|---|---|
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,114,421 A * | 5/1992 | Polak ............... A61J 1/06 604/403 |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,608 A * | 1/1994 | Cherif Cheikh ...... A61M 5/145 604/892.1 |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |

(56) References Cited

U.S. PATENT DOCUMENTS

| | | | |
|---|---|---|---|
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,169 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,621,893 B2 | 11/2009 | Moberg et al. | |
| 7,828,764 B2 | 11/2010 | Moberg et al. | |
| 7,905,868 B2 | 3/2011 | Moberg et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0093192 A1* | 7/2002 | Matkovich | A61M 39/1011 285/3 |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2008/0269682 A1* | 10/2008 | Kavazov | A61M 5/1413 604/126 |
| 2008/0269687 A1 | 10/2008 | Chong et al. | |
| 2008/0294100 A1* | 11/2008 | de Costa | A61K 9/0019 604/84 |
| 2009/0081951 A1 | 3/2009 | Erdmann et al. | |
| 2009/0082635 A1 | 3/2009 | Baldus et al. | |
| 2009/0299290 A1 | 12/2009 | Moberg | |
| 2011/0060274 A1* | 3/2011 | Kuhn | A61M 5/284 604/82 |
| 2012/0035543 A1* | 2/2012 | Kamen | A61M 5/14244 604/113 |
| 2013/0253439 A1* | 9/2013 | Wyss | A61J 1/05 604/246 |
| 2013/0296825 A1* | 11/2013 | Lerner | A61M 5/46 604/506 |
| 2014/0039456 A1* | 2/2014 | Lerner | A61M 5/427 604/506 |
| 2014/0358111 A1* | 12/2014 | Brewer | A61M 5/14244 604/500 |
| 2015/0018765 A1 | 1/2015 | Wong et al. | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| EP | 2455126 A1 | 5/2012 |
| EP | 2623142 A1 | 8/2013 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

(56) References Cited

OTHER PUBLICATIONS

Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump For those who appreciate the difference.
(MiniMed inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.

Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

(56) References Cited

OTHER PUBLICATIONS

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al, "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

SYSTEMS FOR FLUID DELIVERY WITH WICKING MEMBRANE

TECHNICAL FIELD

Embodiments of the subject matter described herein relate generally to fluid infusion devices for delivering a medication fluid to the body of a user. More particularly, embodiments of the subject matter relate to systems for delivering fluid from a fluid reservoir with a wicking membrane.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. In certain instances, during fluid delivery, air may become trapped within the fluid reservoir, which may affect fluid delivery accuracy.

Accordingly, it is desirable to provide systems for fluid delivery from a fluid reservoir with a wicking membrane, which ensures fluid delivery accuracy in instances where air may be trapped within the fluid reservoir. Furthermore, other desirable features and characteristics will become apparent from the subsequent detailed description and the appended claims, taken in conjunction with the accompanying drawings and the foregoing technical field and background.

BRIEF SUMMARY

According to the various teachings of the present disclosure, provided is a fluid reservoir system. The fluid reservoir system includes a fluid reservoir that defines a chamber to receive a fluid, and the fluid reservoir includes an outlet. The fluid reservoir system includes a source of pressure to draw the fluid into the outlet and a wicking membrane is coupled to the fluid reservoir that covers the outlet.

Further provided according to various embodiments is a fluid reservoir system. The fluid reservoir system includes a fluid reservoir that defines a chamber to receive a fluid, and the fluid reservoir includes an outlet that defines a fluid flow path. The fluid reservoir system also includes a source of pressure to dispense the fluid through the outlet. The fluid reservoir system includes a hydrophilic wicking membrane coupled to the fluid reservoir so as to be disposed within the chamber. The wicking membrane completely covers the outlet to substantially prevent a flow of air into the fluid flow path.

Also provided is a fluid infusion device. The fluid infusion device includes a fluid reservoir that defines a chamber to receive a fluid. The fluid reservoir includes a first end and a second end, with an outlet formed at the first end to define a fluid flow path. The fluid infusion device includes a drive system having a portion movable within the chamber to dispense the fluid through the outlet. The fluid infusion device also includes a hydrophilic wicking membrane coupled at the first end of the fluid reservoir so as to be disposed entirely within the chamber. The wicking membrane completely covers the outlet to substantially prevent a flow of air into the fluid flow path.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
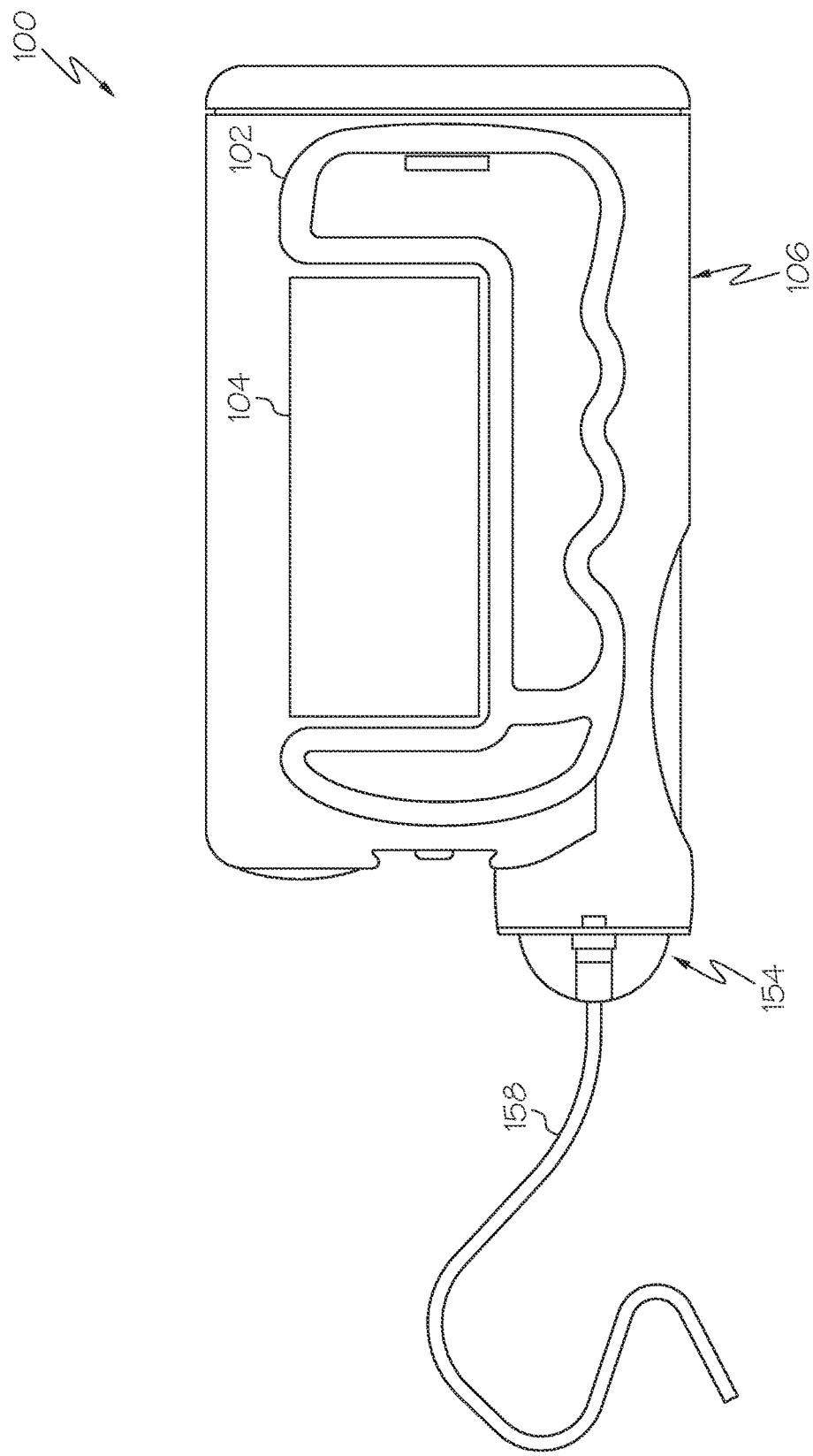
FIG. 1 is a perspective view of an exemplary embodiment of a fluid infusion device for fluid delivery with a wicking membrane according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below"

could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

Figure 1A:
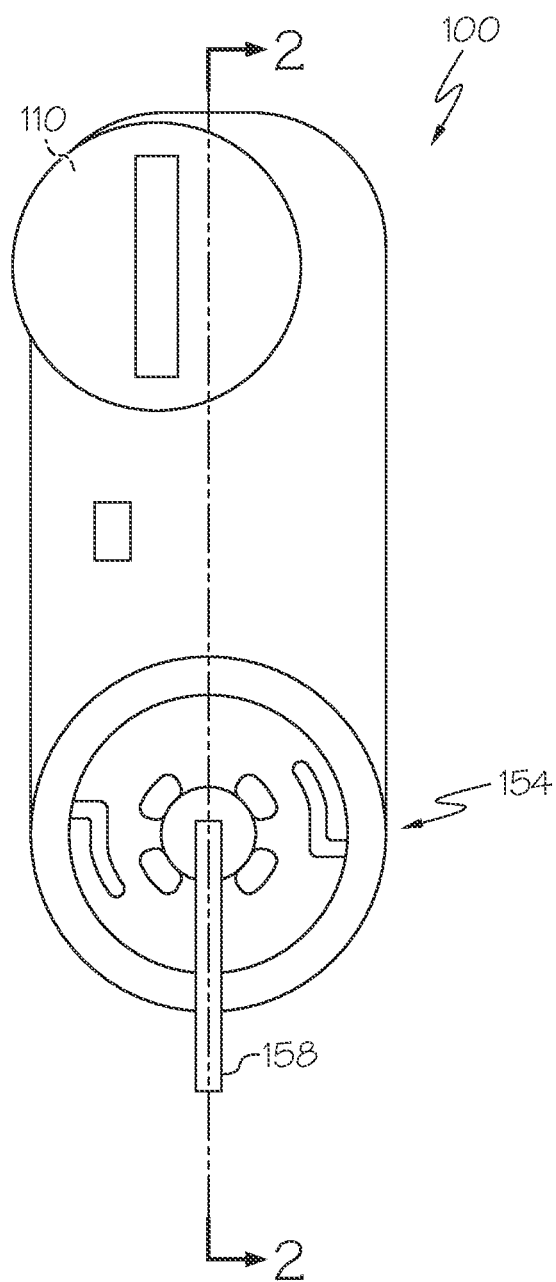
FIG. 1A is a top view of the fluid infusion device of FIG. 1.

FIG. 1 is a perspective view of an exemplary embodiment of a fluid infusion device 100, and FIG. 1A is a top view of the fluid infusion device 100. In this example, the fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

With reference to FIG. 1, the fluid infusion device 100 includes a user interface 102 and a display 104 coupled to a housing 106. The user interface 102 includes one or more user input devices, such as buttons, which can be activated by the user. The user interface 102 can be used to administer a bolus of insulin, to change therapy settings, to change user preferences, to select display features, and the like. Although not required, the illustrated embodiment of the fluid infusion device 100 includes the display 104. The display 104 can be used to present various types of information or data to the user, such as, without limitation: the current glucose level of the patient; the time; a graph or chart of the patient's glucose level versus time; device status indicators; etc. In some embodiments, the display 104 is realized as a touch screen display element and, therefore, the display 104 also serves as a user interface component.

Figure 2:
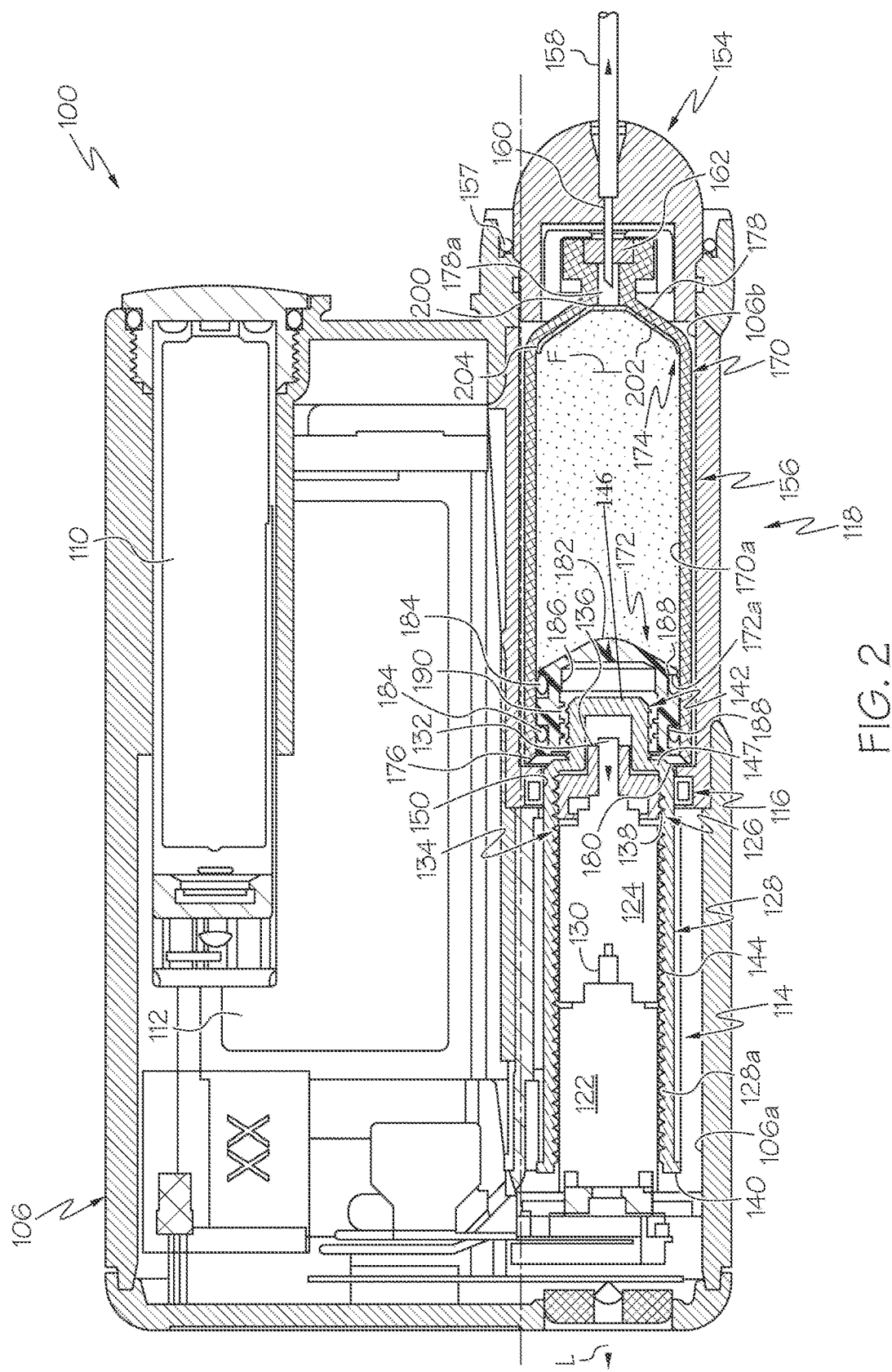
FIG. 2 is cross-sectional view of the fluid infusion device of FIG. 1, taken along line 2-2 of FIG. 1A.

With reference to FIG. 2, the housing 106 of the fluid infusion device 100 accommodates a power supply 110, a controller 112, a drive system 114, a seal 116 and a fluid reservoir system 118. Generally, the power supply 110, the controller 112, the drive system 114 and the seal 116 are accommodated in a pump chamber 106a defined by the housing 106, and the fluid reservoir system 118 is accommodated in a reservoir chamber 106b defined by the housing 106.

The power supply 110 is any suitable device for supplying the fluid infusion device 100 with power, including, but not limited to, a battery. In one example, the power supply 110 is removable relative to the housing 106; however, the power supply 110 may be fixed within the housing 106. The controller 112 is in communication with the user interface 102 (FIG. 1), the display 104 (FIG. 1), the power supply 110 and the drive system 114. The controller 112 controls the operation of the fluid infusion device 100 based on patient specific operating parameters. For example, the controller 112 controls the supply of power from the power supply 110 to the drive system 114 to activate the drive system 114 to dispense fluid from the fluid reservoir system 118. Further detail regarding the control of the fluid infusion device 100 can be found in U.S. Pat. Nos. 6,485,465 and 7,621,893, the relevant content of which was previously incorporated herein by reference.

The drive system 114 cooperates with the fluid reservoir system 118 to dispense the fluid from the fluid reservoir system 118. In one example, the drive system 114 includes a motor 122, a gear box 124, a drive screw 126 and a slide 128. The motor 122 receives power from the power supply 110. In one example, the motor 122 is an electric motor. The motor 122 includes an output shaft 130, which is coupled to the gear box 124. In one embodiment, the gear box 124 is a reduction gear box. The gear box 124 includes an output shaft 132, which is coupled to the drive screw 126.

The drive screw 126 includes a generally cylindrical distal portion 134 and a generally cylindrical proximal portion 136. The distal portion 134 includes a plurality of threads 138. The threads 138 are generally formed about an exterior circumference of the distal portion 134. The proximal portion 136 is generally unthreaded, and is sized to be received within a portion of the slide 128. Thus, the proximal portion 136 serves to align the drive screw 126 within the slide 128 during assembly, for example.

With continued reference to FIG. 2, the slide 128 is substantially cylindrical and includes a distal slide end 140, a proximal slide end 142 and a plurality of threads 144. The distal slide end 140 is adjacent to the motor 122 when the slide 128 is in a first, fully retracted position and the proximal slide end 142 is adjacent to the drive screw 126 when the slide 128 is in the first, fully retracted position. The proximal slide end 142 includes a projection 146 and a shoulder 147, which cooperate with the fluid reservoir system 118 to dispense the fluid from the fluid reservoir system 118. In one example, the projection 146 has a diameter that is smaller than a diameter of a remainder of the slide 128. It should be noted that the use of the projection 146 is merely exemplary, as the slide 128 need not include a projection 146 such that the proximal slide end 142 can be flat or planar. The shoulder 147 is defined adjacent to the projection 146 and contacts a portion of the fluid reservoir system 118 to dispense fluid from the fluid reservoir system 118, as will be discussed in greater detail herein.

The plurality of threads 144 of the slide 128 are formed along an interior surface 128a of the slide 128 between the distal slide end 140 and the proximal slide end 142. Generally, the threads 144 do not extend into the projection 146 of the proximal slide end 142. The threads 144 are formed so as to threadably engage the threads 138 of the drive screw 126. Thus, the rotation of the drive screw 126 causes the linear translation of the slide 128.

In this regard, the slide 128 is generally sized such that in a first, retracted position, the motor 122, the gear box 124 and the drive screw 126 are substantially surrounded by the slide 128. The slide 128 is movable to a second, fully extended position through the operation of the motor 122. The slide 128 is also movable to a plurality of positions between the first, retracted position and the second, fully extended position via the operation of the motor 122. Generally, the operation of the motor 122 rotates the output shaft 130, which is coupled to the gear box 124. The gear box 124 reduces the torque output by the motor 122, and the output shaft 132 of the gear box 124 rotates the drive screw 126, which moves along the threads 144 formed within the slide 128. The movement or rotation of the drive screw 126 relative to the slide 128 causes the movement or linear translation of the slide 128 within the housing 106. The advancement of the slide 128 into a portion of the fluid reservoir system 118 causes the fluid reservoir system 118 to dispense fluid.

With reference to FIG. 2, the seal 116 is disposed adjacent to the slide 128 and the reservoir chamber 106b. The seal 116 serves to separate the pump chamber 106a of the housing 106 from the reservoir chamber 106b to prevent the ingress of fluids to the motor 122, the gear box 124 and the drive screw 126 of the drive system 114. Generally, the seal 116 is positioned circumferentially about the slide 128 and defines an opening 150 through which the slide 128 moves.

The fluid reservoir system 118 includes a reservoir cap or connector body 154 and a fluid reservoir 156. The connector body 154 creates a fluid path from the fluid reservoir 156 to the body of the patient. In one exemplary embodiment, the connector body 154 is removably coupled to the housing 106, through any suitable technique, such as threads, press-fitting, etc. Generally, the connector body 154 is suitably sized and configured to accommodate the replacement of fluid reservoirs 156 (which are typically disposable) as needed. A sealing member, such as an O-ring 157 may be coupled between the connector body 154 and the reservoir chamber 106b to prevent the ingress of fluids into the reservoir chamber 106b of the housing 106.

In one example, the connector body 154 accommodates the fluid path from the fluid reservoir 156 to a tubing 158. The tubing 158 represents the fluid flow path that couples the fluid reservoir 156 to an infusion unit to deliver the fluid to the patient (not shown). In one example, the tubing 158 is coupled to the fluid reservoir 156 via a connector needle 160, which is coupled to the connector body 154 and pierces a septum 162 associated with the fluid reservoir 156. It should be noted, however, that any suitable technique could be employed to create a fluid path from the fluid reservoir 156 to the patient, and thus, this embodiment is merely an example.

In one example, the fluid reservoir 156 includes a body or barrel 170, a stopper 172 and a wicking membrane 174. The barrel 170 has a first or distal barrel end 176 and a second or proximal barrel end 178. The barrel 170 defines a fluid chamber for retaining the fluid F. The fluid F is retained within the barrel 170 between the distal barrel end 176 and the proximal barrel end 178. The distal barrel end 176 is positioned adjacent to the slide 128 when the fluid reservoir 156 is assembled in the housing 106. Generally, the distal barrel end 176 has an open perimeter or is circumferentially open such that the slide 128 is receivable within the barrel 170 through the distal barrel end 176. The proximal barrel end 178 defines a port 178a, which receives the connector needle 160 to establish the fluid flow path. The proximal barrel end 178 has any desired shape that mates with at least a portion of the connector body 154.

The stopper 172 is disposed within the barrel 170. The stopper 172 is movable within and relative to the barrel 170 to dispense fluid from the fluid reservoir 156. Stated another way, the stopper 172 is movable within the barrel 170 to pressurize the fluid such that the fluid flows from the barrel 170 through the port 178a into the connector needle 160 and the tubing 158. Thus, the stopper 172 and the drive system 114 cooperate to form a source of pressure for the fluid reservoir system 118. When the barrel 170 is full of fluid, the stopper 172 is adjacent to the distal barrel end 176, and the stopper 172 is movable to a position adjacent to the proximal barrel end 178 to empty the fluid from the fluid reservoir 156. In one example, the stopper 172 is substantially cylindrical, and includes a distal stopper end 180, a proximal stopper end 182, at least one friction element 184 and a counterbore 186 defined from the distal stopper end 180 to the proximal stopper end 182.

The distal stopper end 180 is open about a perimeter of the distal stopper end 180, and thus, is generally circumferentially open. The proximal stopper end 182 is closed about a perimeter of the proximal stopper end 182 and is generally circumferentially closed. The proximal stopper end 182 includes a slightly conical external surface; however, the proximal stopper end 182 can be flat, convex, etc. The at least one friction element 184 is coupled to the stopper 172 about an exterior surface 172a of the stopper 172. In one example, the at least one friction element 184 comprises two friction elements, which include, but are not limited to, O-rings. The friction elements 184 are coupled to circumferential grooves 188 defined in the exterior surface 172a of the stopper 172.

The counterbore 186 receives the projection 146 of the slide 128 and the movement of the slide 128 causes the shoulder 147 of the slide 128 to contact and move the stopper 172. In one example, the counterbore 186 includes threads 190; however, the projection 146 of the slide 128 is not threadably engaged with the stopper 172. Thus, the threads 190 illustrated herein are merely exemplary.

The wicking membrane 174 is coupled within the barrel 170 of the fluid reservoir 156. The wicking membrane 174 is generally coupled to the barrel 170 so as to completely cover an outlet 200 in the barrel 170 defined by the port 178a. The wicking membrane 174 completely covers the outlet 200 to substantially prevent the flow of air into the fluid flow path defined by the outlet 200, the port 178a and the tubing 158. In this example, the wicking membrane 174 is coupled to the barrel 170 at the proximal barrel end 178 such that the entirety of the wicking membrane 174 is disposed in the fluid chamber defined within the barrel 170. It will be understood, however, that the wicking membrane 174 may be coupled to the fluid reservoir 156 such that only the outlet 200 is covered by the wicking membrane 174. Moreover, it should be understood that the wicking membrane 174 may be coupled to the barrel 170 so as to extend from the proximal barrel end 178 to a point located between the proximal barrel end 178 and the distal barrel end 176, if desired. Thus, the wicking membrane 174 as illustrated herein is merely an example.

The wicking membrane 174 includes a first surface 202 substantially opposite a second surface 204. The first surface 202 is disposed within the barrel 170 so as to be in contact with and wetted by the fluid F. The second surface 204 is coupled to an interior surface 170a of the barrel 170 via any suitable technique, such as ultrasonic welding, adhesives, thermal bonding, mechanical fastening (e.g. staples, stitches), etc. Generally, the wicking membrane 174 is coupled to the barrel 170 so as to be fixedly or non-removably coupled to the barrel 170. The wicking membrane 174 may have a substantially small thickness, such as about 0.0762 millimeters (mm) or about 0.003 inches (in.). In this example, the wicking membrane 174 is coupled at the proximal barrel end 178 to enable the stopper 172 to be advanced to the proximal barrel end 178 without contact between the one or more friction elements 184 and the wicking membrane 174. It will be understood, however, that the stopper 172 may be configured to be advanced over a portion of the wicking membrane 174, if desired.

In one example, the wicking membrane 174 is a hydrophilic wicking membrane that draws the fluid F towards the outlet 200 via capillary action. The wicking membrane 174 enables the fluid F to flow from the barrel 170 through the port 178a, while inhibiting or preventing air from exiting through the port 178a. Thus, the wicking membrane 174 may comprise any suitable membrane that enables the passage of a liquid, such as the fluid F, through the membrane via capillary action, while substantially inhibiting the passage of air through the membrane. The first surface 202 of the wicking membrane 174, when wetted by the fluid F, draws the fluid F up through the wicking membrane 174 across a small volume of air due to the surface tension of the fluid F. The first surface 202 may be wetted by the fluid F within the fluid reservoir 156 during the normal use and operation of the fluid reservoir 156.

A pressure difference between the barrel 170 and the tubing 158 also assists the wicking membrane 174 in drawing the liquid or fluid F within the barrel 170 to the port 178a. In this regard, as a pressure within the barrel 170 is higher than a pressure in the tubing 158, the fluid F in the barrel 170 in contact with the first surface 202 of the wicking membrane 174 will be drawn up through the wicking membrane 174 via capillary action through the outlet 200 and out the port 178a.

The wicking membrane 174 may have any suitable pore size to assist in drawing the fluid F through the first surface 202 of the wicking membrane 174 while inhibiting the passage of air through the wicking membrane 174. In one example, the pore size ranges from about 0.1 micrometers (μm) to about 35.0 micrometers (μm). It should be noted that the wicking membrane 174 may have any desired pore size, and moreover, that the pore size may vary over portions of the wicking membrane 174 if desired. Generally, as the average pore size for the wicking membrane 174 decreases, the pressure differential between the barrel 170 and the port 178a required to disrupt the wetted first surface 202 increases (which decreases the likelihood of the introduction of air into the port 178a) and for a given pressure differential the flow rate of the fluid F through the wicking membrane 174 decreases. Thus, the pore size of the wicking membrane 174 may be dependent on the pressure differential between the fluid reservoir 156 and the tubing 158, the surface tension of the fluid F and a desired flow rate for the fluid F. The pore size selected for the wicking membrane 174 may also be dependent on the viscosity of the fluid F, the density of the fluid F, the surface angle between the wicking membrane 174 and the fluid F and the height of the port 178a above a surface of the fluid F. An exemplary hydrophilic wicking membrane 174 for use with the fluid reservoir 156 may comprise about a 0.330 millimeter (mm) or about 0.013 inches (in.) thick fiber membrane with an average pore size of about 5.0 micrometers (μm).

It should be noted that while the wicking membrane 174 is described and illustrated herein as comprising a membrane, the wicking membrane 174 need not be a membrane. In this regard, a series of micro-channels having hydrophilic inner surfaces may be defined or formed in the barrel 170 near the outlet 200. Thus, the wicking membrane 174 is merely an example.

With continued reference to FIG. 2, with the housing 106 assembled with the power supply 110, the controller 112 and the drive system 114, the fluid reservoir system 118 is coupled to the housing 106 with the wicking membrane 174 coupled at the proximal barrel end 178. Generally, a full fluid reservoir 156 is inserted into the reservoir chamber 106b of the housing 106 such that the stopper 172 is adjacent to the projection 146 of the slide 128. As the drive screw 126 rotates, the slide 128 translates linearly. The advancement of the slide 128 decreases an available volume within the barrel 170, which results in an increase in pressure in the barrel 170.

Figure 3:
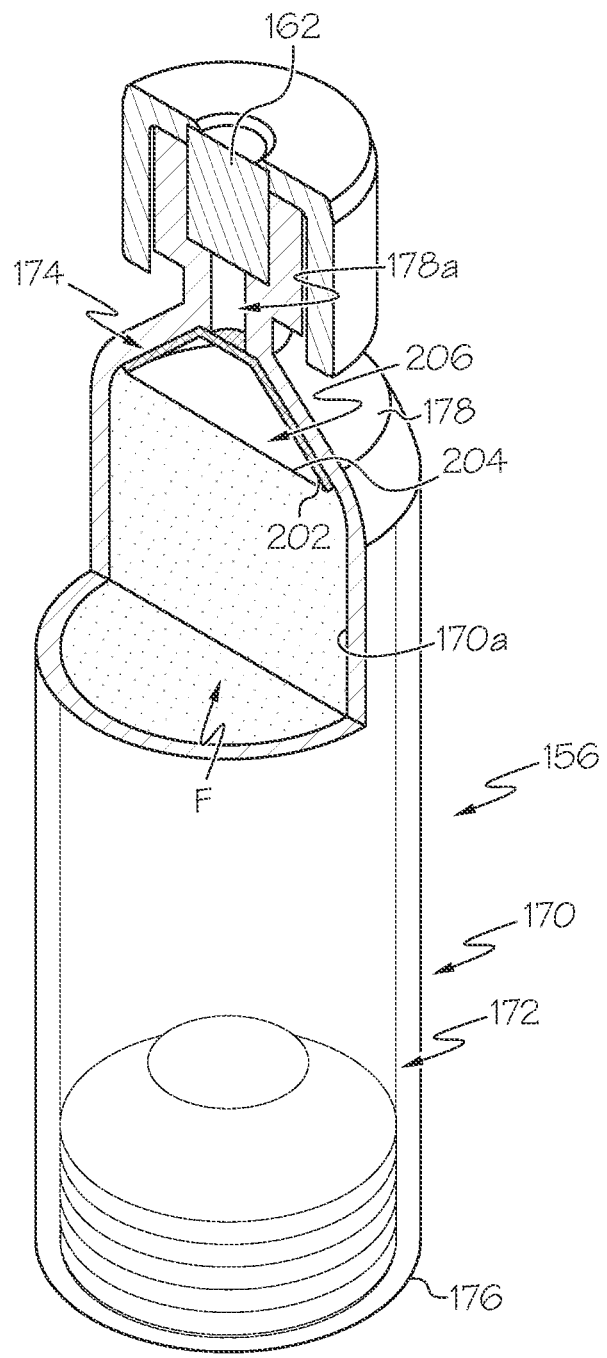
FIG. 3 is a perspective, partially cut-away view of a portion of a fluid reservoir system of the fluid infusion device of FIG. 1 according to an exemplary embodiment.

The pressure increase in the barrel 170 causes a pressure differential between the fluid reservoir 156 and the tubing 158, which is generally at an ambient pressure. The pressure differential assists in dispensing fluid F from the barrel 170 by drawing the fluid F into the tubing 158. Thus, the pressure increase in the barrel 170 acts as a source of positive pressure on the fluid reservoir 156 to draw the fluid into the outlet 200 and cooperates with the wicking membrane 174 to dispense the fluid F from the fluid reservoir 156 with substantially no air entering the outlet 200. With reference to FIG. 3, the pressure differential also assists the wicking membrane 174 in wicking the fluid F over air 206 disposed or trapped within the barrel 170. In this regard, with the second surface 204 coupled to the barrel 170 at the proximal barrel end 178 such that the wicking membrane 174 covers the outlet 200 and the fluid F in contact with the first surface 202, the fluid F may be drawn up into the outlet 200 via the capillary action of the wicking membrane 174. The surface tension of the fluid F enables the fluid F to flow out of the outlet 200 into the port 178a with substantially none of the air 206 exiting the barrel 170. By preventing the air 206 from exiting the fluid reservoir 156, the wicking membrane 174 improves fluid volume delivery accuracy. Thus, the fluid reservoir system 118 enables the fluid F in the fluid reservoir 156 to bypass the air 206 trapped in the barrel 170 such that substantially little to no air enters the fluid flow path defined by the connector needle 160 and tubing 158.

Figure 4:
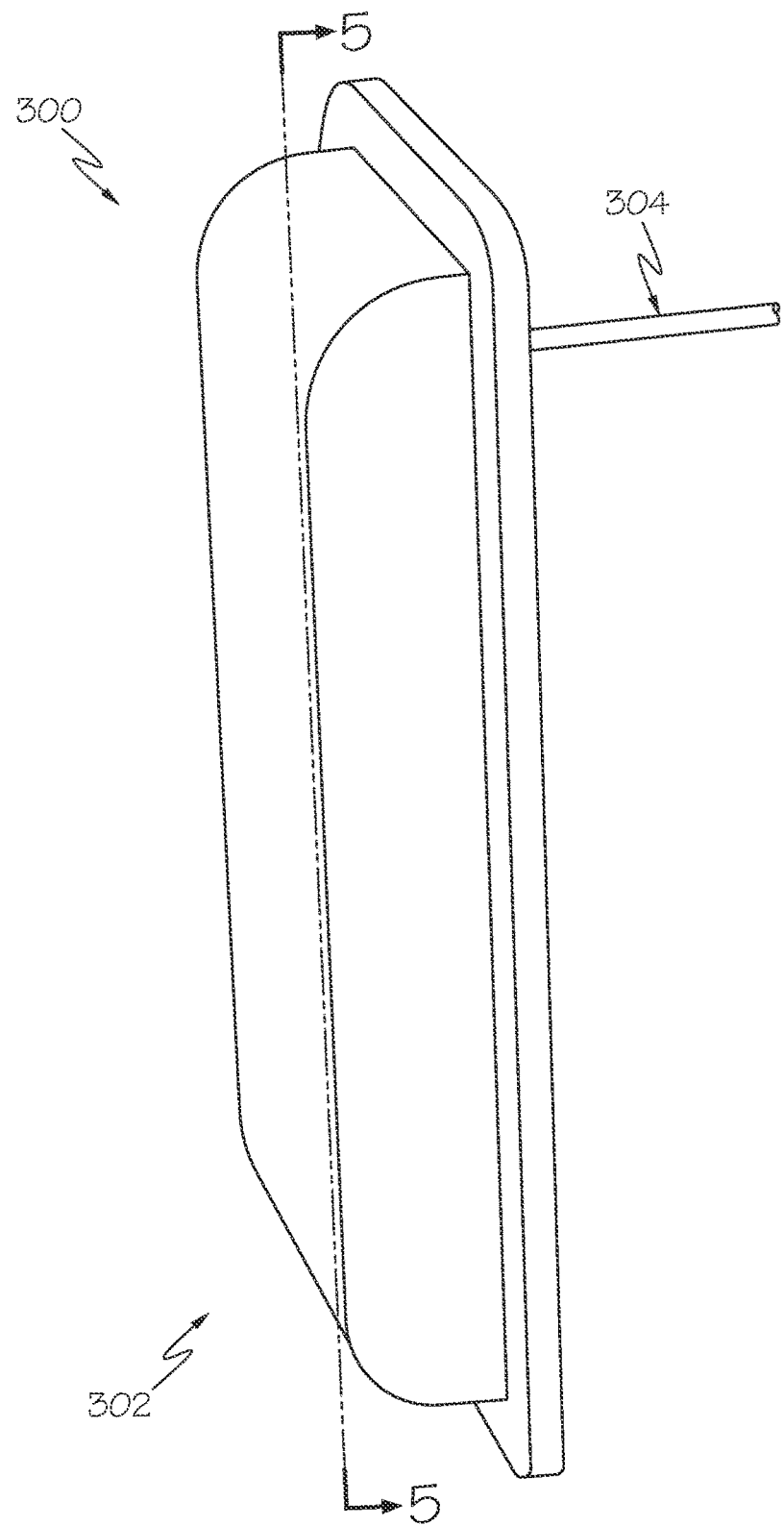
FIG. 4 is a perspective view of an exemplary embodiment of a fluid infusion device for fluid delivery with a wicking membrane according to various teachings of the present disclosure.
Figure 5:
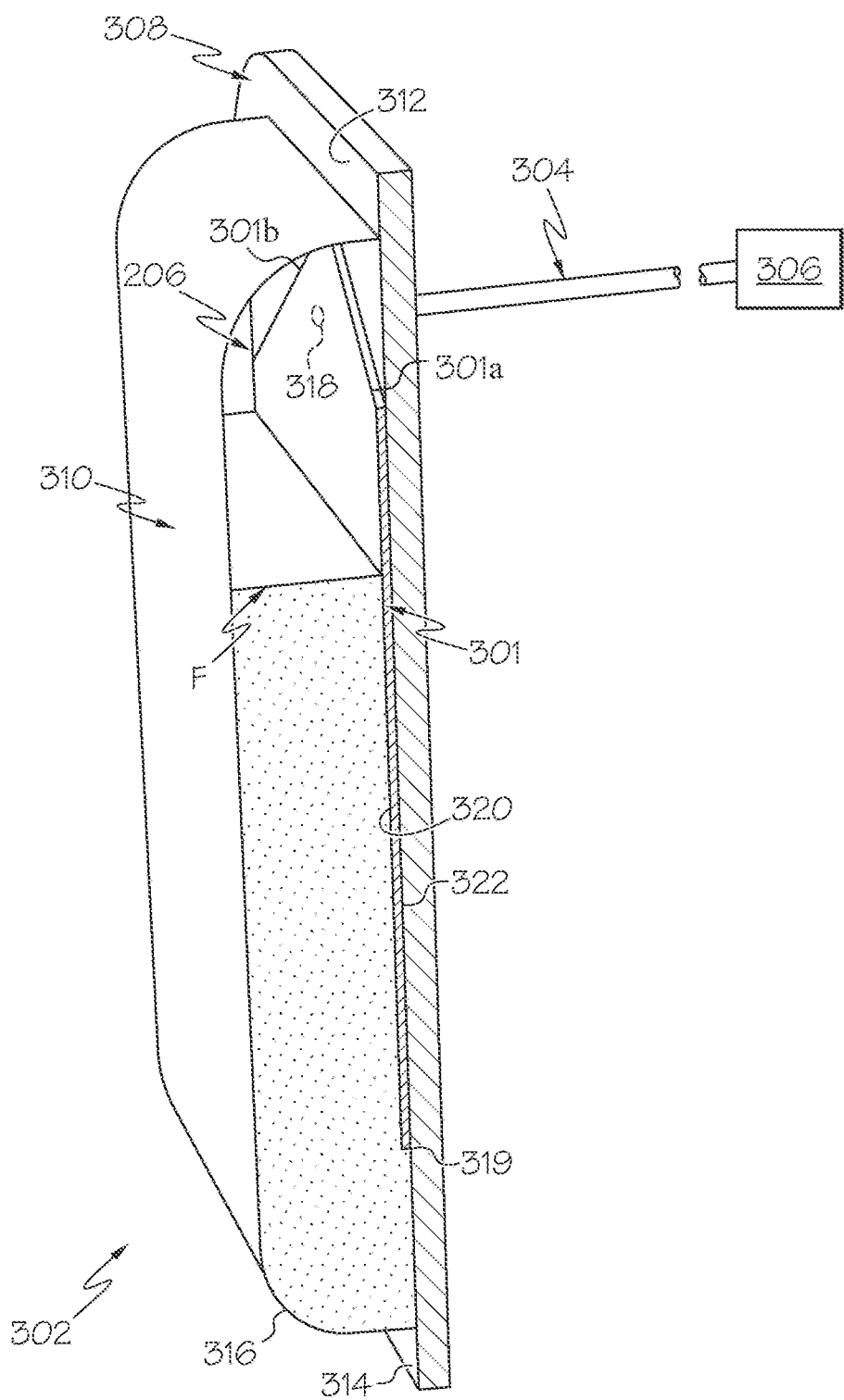
FIG. 5 is a cross-sectional view of the fluid infusion device of FIG. 4, taken along line 5-5 of FIG. 4.

With reference now to FIGS. 4 and 5, a fluid reservoir system 300 is shown. As the fluid reservoir system 300 may be similar to the fluid reservoir system 118 discussed with regard to FIGS. 1-3, the same reference numerals will be used to denote the same or similar components.

In this example, the fluid reservoir system 300 comprises a semi-flexible fluid reservoir 302, which may employ a wicking membrane 301 (FIG. 5) similar to the wicking membrane 174 of FIGS. 1-3. The fluid reservoir 302 is operable to dispense fluid F or create a fluid flow path from the fluid reservoir 302 through a suitable hollow tubing 304. As discussed with regard to FIGS. 1-3, the fluid dispensed by the fluid reservoir system 300 may comprise any suitable fluid, including, but not limited to, disease treatments, drugs to treat pulmonary hypertension, iron chelation drugs, pain medications, anti-cancer treatments, medications, vitamins, hormones, insulin or the like. The fluid reservoir system 300 may comprise a stand-alone system for the dispensing of fluid to a patient, or may comprise a portion of a fluid infusion device.

In one example, with reference to FIG. 5, the tubing 304 is coupled to a source of pressure to draw the fluid from the fluid reservoir 302. For example, the tubing 304 is coupled to a source of a negative pressure 306, which creates a pressure differential between the fluid reservoir 302 and the tubing 304 to draw the fluid into the tubing 304. The source of negative pressure 306 may comprise any suitable negative pressure source, such as an in-line pumping system, including, but not limited to a peristaltic pump, a piston pump or the like. A suitable coupling or infusion set may be fluidly coupled downstream from the source of negative pressure 306 to deliver the fluid F to a patient, for example.

In this example, the fluid reservoir 302 includes a first, rigid reservoir wall 308 and a second, flexible reservoir wall 310. The rigid reservoir wall 308 may be composed of any suitable material, for example, a biocompatible polymeric material. The second, flexible reservoir wall 310 may be composed of a suitable flexible material, or a material that has greater flexibility than that of the rigid reservoir wall 308, including, but not limited to a flexible biocompatible material, such as a biocompatible polymer. The flexible reservoir wall 310 is coupled to the rigid reservoir wall 308 between a first or proximal end 312 and a second or distal end 314 of the rigid reservoir wall 308. Generally, the flexible reservoir wall 310 is coupled to the rigid reservoir wall 308 so as to define a fluid chamber 316. It should be noted that while the fluid reservoir 302 is illustrated herein as comprising the rigid reservoir wall 308 and the flexible reservoir wall 310, the fluid reservoir 302 may comprise any number of walls to define a fluid chamber. The fluid chamber 316 receives and contains the fluid F for dispensing.

The rigid reservoir wall 308 also includes an outlet 318. The outlet 318 is defined through the rigid reservoir wall 308 so as to enable fluid communication between the tubing 304 and the fluid chamber 316. The wicking membrane 301 is coupled to the rigid reservoir wall 308 so as to completely cover the outlet 318. The wicking membrane 301 completely covers the outlet 318 to substantially prevent the flow of air 206 into the fluid flow path defined by the outlet 318 and the tubing 304. In this example, the wicking membrane 301 extends from the proximal end 312 of the rigid reservoir wall 308 to a point 319 located near the distal end 314. The wicking membrane 301 is coupled to the rigid reservoir wall 308 such that the entirety of the wicking membrane 301 is disposed in the fluid chamber 316. By covering substantially an entirety of the rigid reservoir wall 308, the wicking membrane 301 assists in wicking the fluid F when the fluid chamber 316 has a low fluid level.

The wicking membrane 301 is coupled to the rigid reservoir wall 308 within the fluid chamber 316. The wicking membrane 301 includes a first surface 320 substantially opposite a second surface 322. The first surface 320 is disposed within the fluid chamber 316 so as to be in contact with and wetted by the fluid F. The second surface 322 is coupled to the rigid reservoir wall 308 via any suitable technique, such as ultrasonic welding, adhesives, thermal bonding, mechanical fastening (e.g. staples, stitches), etc. Generally, the wicking membrane 301 is coupled to the rigid reservoir wall 308 so as to be fixedly or non-removably coupled to the rigid reservoir wall 308. The wicking membrane 301 may also include one or more contours 301a, 301b formed at a first end of the wicking membrane 301 or formed to be adjacent to the outlet 318 when the wicking membrane 301 is coupled to the outlet 318. The contours 301a, 301b may assist in directing a flow of the fluid F from the fluid chamber 316 to the outlet 318.

In one example, the wicking membrane 301 is a hydrophilic wicking membrane that draws fluid via capillary action. The wicking membrane 301 enables the fluid F to flow from the fluid chamber 316 through the outlet 318, while inhibiting or preventing air from exiting through the outlet 318. Thus, the wicking membrane 301 may comprise any suitable membrane that enables the passage of a liquid, such as the fluid F, through the membrane via capillary action, while substantially inhibiting the passage of air through the membrane. The first surface 320 of the wicking membrane 301, when wetted by the fluid F, draws the fluid F up through the wicking membrane 301 across a small volume of air due to the surface tension of the fluid F. The first surface 320 may be wetted by the fluid F within the fluid chamber 316 during the normal use and operation of the fluid chamber 316.

Generally, the pressure difference between the fluid chamber 316 and the tubing 304 created by the source of negative pressure 306 assists the wicking membrane 301 in drawing the liquid or fluid F within the fluid chamber 316 to the outlet 318. In this regard, as a pressure within the fluid chamber 316 is greater than a pressure in the tubing 304, the fluid F in the fluid chamber 316 in contact with the first surface 320 of the wicking membrane 301 will be drawn up through the wicking membrane 301 and out the outlet 318 into the tubing 304. Thus, the source of negative pressure 306 acts on the fluid reservoir 302 to draw the fluid F into the outlet 318 and cooperates with the wicking membrane 301 to dispense the fluid F from the fluid reservoir 302 with substantially no air entering the outlet 318.

The wicking membrane 301 may have any suitable pore size to assist in drawing the fluid F through the first surface 320 of the wicking membrane 301 while inhibiting the passage of air through the wicking membrane 301. In one example, the pore size ranges from about 0.1 micrometers ($\mu m$) to about 35.0 micrometers ($\mu m$). It should be noted that the wicking membrane 301 may have any desired pore size, and moreover, that the pore size may vary over portions of the wicking membrane 301 if desired. Thus, the pore size of the wicking membrane 301 may be dependent on the pressure differential between the fluid chamber 316 and the tubing 304, the surface tension of the fluid F and a desired flow rate for the fluid F. The pore size selected for the wicking membrane 301 may also be dependent on the viscosity of the fluid F, the density of the fluid F, the surface angle between the wicking membrane 301 and the fluid F and the height of the outlet 318 above a surface of the fluid F. An exemplary hydrophilic wicking membrane 301 for use with the fluid chamber 316 may comprise about a 0.330 millimeter (mm) or about 0.013 inches (in.) thick fiber membrane with an average pore size of about 5.0 micrometers ($\mu m$).

It should be noted that while the wicking membrane 301 is described and illustrated herein as comprising a membrane, the wicking membrane 301 need not be a membrane. In this regard, a series of micro-channels having hydrophilic inner surfaces may be defined or formed on the rigid reservoir wall 308 near the outlet 318. Thus, the wicking membrane 301 is merely an example.

With the fluid reservoir system 300 assembled, and the fluid F disposed within the fluid chamber 316, the source of negative pressure 306 applies a negative pressure to the tubing 304. The negative pressure creates a pressure differential between the fluid chamber 316 and the tubing 304. The pressure differential assists in drawing the fluid F up through the wicking membrane 301, through the outlet 318 and into the tubing 304 and prevents substantially all of the air 206 from entering the outlet 318.

Figure 6:
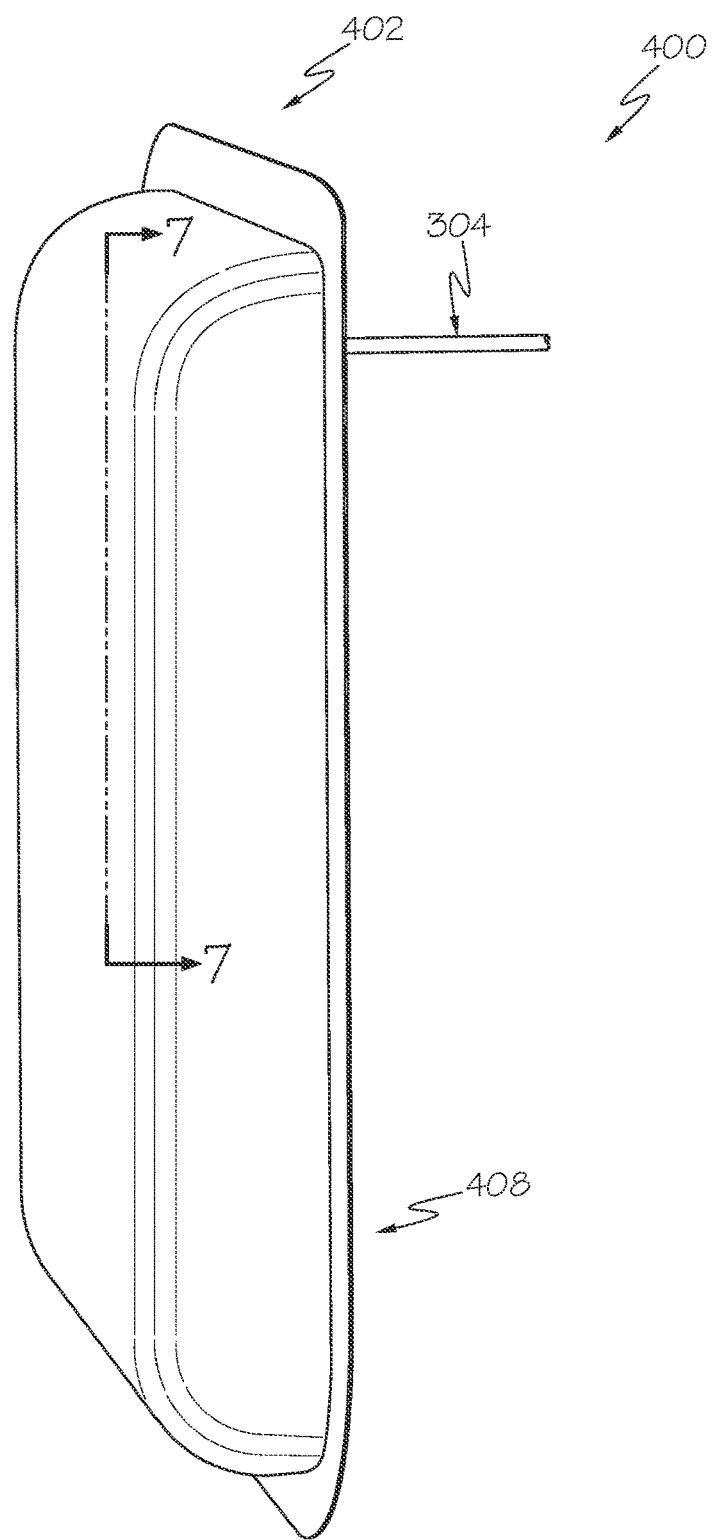
FIG. 6 is a perspective view of an exemplary embodiment of a fluid infusion device for fluid delivery with a wicking membrane according to various teachings of the present disclosure.
Figure 7:
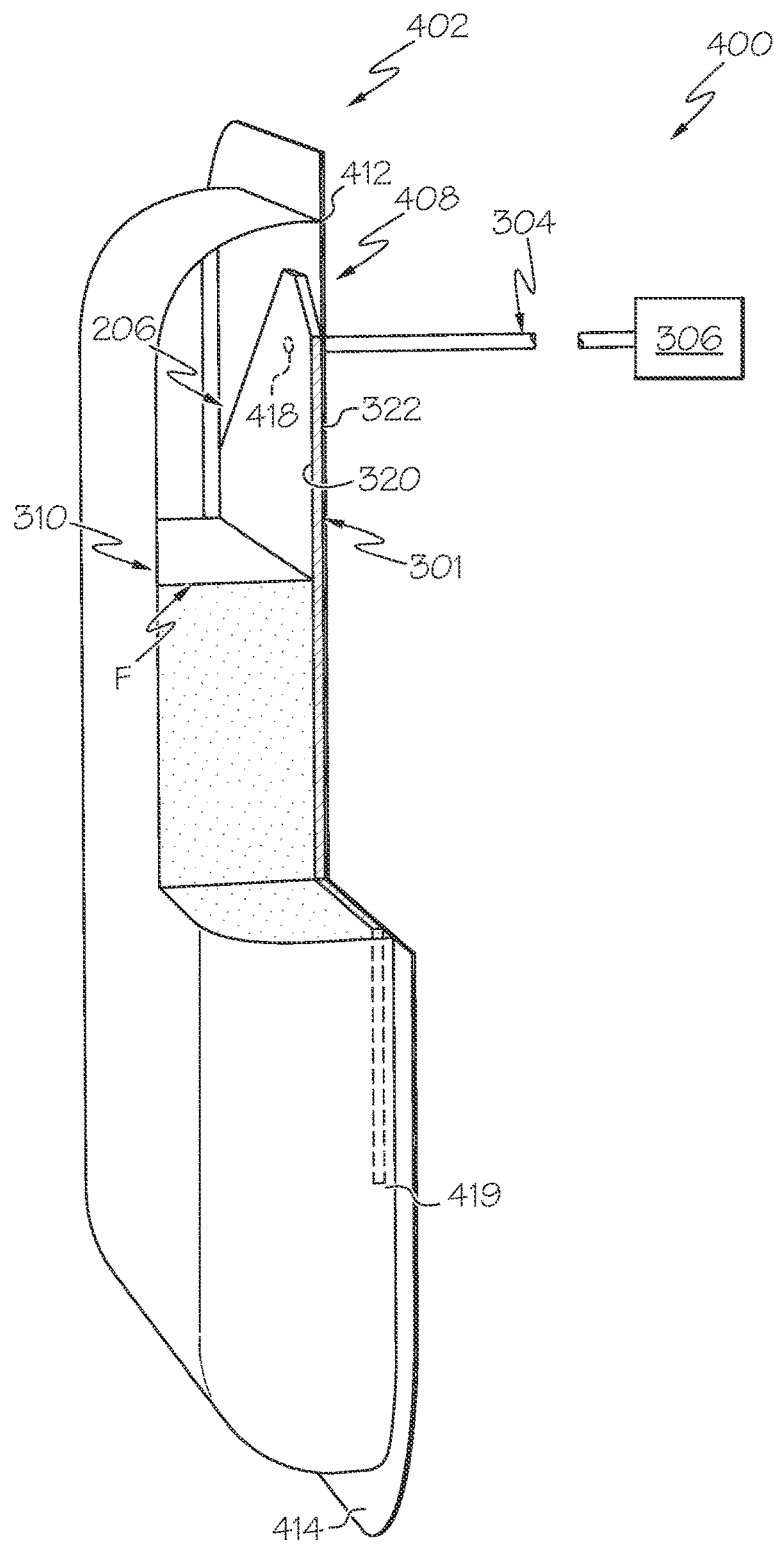
FIG. 7 is a cross-sectional view of the fluid infusion device of FIG. 6, taken along line 7-7 of FIG. 6.

With reference now to FIGS. 6 and 7, a fluid reservoir system 400 is shown. As the fluid reservoir system 400 may be similar to the fluid reservoir system 300 discussed with regard to FIGS. 4 and 5, the same reference numerals will be used to denote the same or similar components.

In one example, the fluid reservoir system 400 comprises a fully flexible fluid reservoir 402, which may employ the wicking membrane 301. The fluid reservoir 402 is operable to dispense fluid F or create a fluid flow path from the fluid reservoir 402 through the tubing 304. The fluid dispensed by the fluid reservoir system 400 may comprise any suitable fluid, including, but not limited to, disease treatments, drugs to treat pulmonary hypertension, iron chelation drugs, pain medications, anti-cancer treatments, medications, vitamins, hormones, insulin or the like. The fluid reservoir system 400 may comprise a stand-alone system for the dispensing of fluid to a patient, or may comprise a portion of a fluid infusion device.

In one example, with reference to FIG. 7, the tubing 304 is coupled to the source of a negative pressure 306, which creates a pressure differential between the fluid reservoir 402 and the tubing 304. A suitable coupling or infusion set may be fluidly coupled downstream from the source of negative pressure 306 to deliver the fluid F to a patient, for example.

In this example, the fluid reservoir 402 includes a first, flexible reservoir wall 408 and the second, flexible reservoir wall 310. The first, flexible reservoir wall 408 and the second, flexible reservoir wall 310 may be composed of any suitable flexible material, for example, a flexible biocompatible polymeric material. The second, flexible reservoir wall 310 is coupled to the first, flexible reservoir wall 408 between a first or proximal end 412 and a second or distal end 414 of the first, flexible reservoir wall 408. Generally, the second, flexible reservoir wall 310 is coupled to the first, flexible reservoir wall 408 so as to define the fluid chamber 316. It should be noted that while the fluid reservoir 402 is illustrated herein as comprising the first, flexible reservoir wall 408 and the second, flexible reservoir wall 310, the fluid reservoir 402 may comprise any number of walls to define a fluid chamber. The fluid chamber 316 receives and contains the fluid F for dispensing.

The first, flexible reservoir wall 408 also includes an outlet 418. The outlet 418 is defined through the first, flexible reservoir wall 408 so as to enable fluid communication between the tubing 304 and the fluid chamber 316. The wicking membrane 301 is coupled to the first, flexible reservoir wall 408 so as to completely cover the outlet 418. The wicking membrane 301 completely covers the outlet 418 to substantially prevent the flow of air 206 into the fluid flow path defined by the outlet 418 and the tubing 304. The wicking membrane 301 is coupled to the first, flexible reservoir wall 408 such that the entirety of the wicking membrane 301 is disposed in the fluid chamber 316. In this example, the wicking membrane 301 extends from the proximal end 412 of the first, flexible reservoir wall 408 to a point 419 located near the distal end 414. By covering substantially an entirety of the first, flexible reservoir wall 408, the wicking membrane 301 assists in wicking the fluid F when the fluid chamber 316 has a low fluid level.

The wicking membrane 301 is coupled to the first, flexible reservoir wall 408 within the fluid chamber 316. The first surface 320 is disposed within the fluid chamber 316 so as to be in contact with and wetted by the fluid F. The second surface 322 is coupled to the first, flexible reservoir wall 408 via any suitable technique, such as ultrasonic welding, adhesives, thermal bonding, mechanical fastening (e.g. staples, stitches), etc. Generally, the wicking membrane 301 is coupled to the first, flexible reservoir wall 408 so as to be fixedly or non-removably coupled to the first, flexible reservoir wall 408. The wicking membrane 301 may also include the one or more contours 301a, 301b.

The wicking membrane 301 enables the fluid F to flow from the fluid chamber 316 through the outlet 418, while inhibiting or preventing air from exiting through the outlet 418. With the fluid reservoir system 400 assembled, and the fluid F disposed within the fluid chamber 316, the source of negative pressure 306 applies a negative pressure to the tubing 304. The negative pressure creates a pressure differential between the fluid chamber 316 and the tubing 304. The pressure differential assists in drawing the fluid F up through the wicking membrane 301, through the outlet 418 and into the tubing 304. Thus, the source of negative pressure 306 acts on the fluid reservoir 402 to draw the fluid F into the outlet 418 and cooperates with the wicking membrane 301 to dispense the fluid F from the fluid reservoir 402 with substantially no air entering the outlet 418. The wicking membrane 301 prevents substantially all of the air 206 from entering the outlet 418, and thereby improves fluid volume delivery accuracy.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device, comprising:
a housing having a first chamber and a second chamber, with a seal that separates the first chamber from the second chamber, and the seal defines an opening;
a fluid reservoir removably received within the second chamber of the housing that defines a reservoir chamber to receive a fluid, the fluid reservoir including a first end and a second end, the first end having an open perimeter and the second end terminates in a port that includes an outlet, the fluid reservoir including a stopper disposed in the reservoir chamber that is movable from the first end to the second end to dispense the fluid through the outlet and the stopper has a distal stopper end opposite a proximal stopper end, with a counterbore defined through the distal stopper end, the fluid reservoir having a first pressure;
a drive system received within the first chamber of the housing having a slide, a motor, a gear box and a drive screw, at least the gear box and the drive screw surrounded by the slide, the motor drives the gear box to rotate the drive screw, the slide including a plurality of threads defined on an interior surface that threadably engage threads of the drive screw such that a rotation of the drive screw by the gear box translates the slide through the opening of the seal into the second chamber, the slide received within the reservoir chamber through the first end of the fluid reservoir and translatable within the reservoir chamber, the slide having a projection received within the counterbore of the stopper and a shoulder that contacts the stopper to move the stopper from the first end to the second end to dispense the fluid into the outlet;

a wicking membrane having a first surface in contact with the fluid and an opposite second surface, the second surface coupled to an interior surface of the fluid reservoir at the second end such that the wicking membrane completely covers the outlet to substantially prevent a flow of air into the outlet and the wicking membrane is spaced apart from the distal stopper end when the stopper is moved to the second end; and a reservoir cap removably coupled to the second chamber of the housing and including a connector needle received within the port downstream of the wicking membrane to define a fluid flow path from the fluid reservoir to a tubing, the tubing having a second pressure, the first pressure greater than the second pressure, and the difference between the first pressure and the second pressure cooperates with the wicking membrane to dispense the fluid through the outlet, wherein the stopper includes at least one friction element that contacts an interior surface of the fluid reservoir and the wicking membrane is coupled to the second end such that the at least one friction element is spaced apart from the wicking membrane when the stopper is moved to the second end.

2. The fluid infusion device of claim 1, wherein the wicking membrane is a hydrophilic membrane.

3. A fluid infusion device, comprising:
a housing having a first chamber and a second chamber, with a seal that separates the first chamber from the second chamber, and the seal defines an opening;
a fluid reservoir received within the second chamber of the housing that defines a reservoir chamber to receive a fluid, the fluid reservoir including a first end and a second end, the first end having an open perimeter and the second end terminates in a port that includes an outlet that defines a fluid flow path, the fluid reservoir including a stopper disposed in the reservoir chamber that is movable from the first end to the second end to dispense the fluid through the outlet, the stopper including at least one friction element that contacts an interior surface of the fluid reservoir, the fluid reservoir having a first pressure;
a drive system received within the first chamber of the housing having a slide, a motor, a gear box and a drive screw, at least the gear box and the drive screw surrounded by the slide, the motor drives the gear box to rotate the drive screw, the slide including a plurality of threads defined on an interior surface that threadably engage threads of the drive screw such that a rotation of the drive screw by the gear box translates the slide through the opening of the seal into the second chamber, the slide received within the reservoir chamber through the first end of the fluid reservoir, the slide translatable within the reservoir chamber, the slide having a projection received within a counterbore of the stopper and a shoulder that contacts the stopper to move the stopper from the first end to the second end to dispense the fluid through the outlet;
a hydrophilic wicking membrane having a first surface in contact with the fluid and an opposite second surface, the second surface coupled to the interior surface of the fluid reservoir at the second end so as to be disposed entirely within the reservoir chamber, the hydrophilic wicking membrane coupled to the second end such that the at least one friction element is spaced apart from the hydrophilic wicking membrane when the stopper is moved to the second end and the hydrophilic wicking membrane is coupled to the interior surface at the second end of the fluid reservoir to completely cover the outlet and substantially prevent a flow of air into the fluid flow path; and a reservoir cap removably coupled to the second chamber of the housing and including a connector needle received within the port such that the connector needle is downstream of the hydrophilic wicking membrane to define a fluid flow path from the fluid reservoir to a tubing, the tubing having a second pressure, the first pressure greater than the second pressure and the difference between the first pressure and the second pressure cooperates with the hydrophilic wicking membrane to dispense the fluid through the outlet.

4. The fluid infusion device of claim 3, wherein the fluid is insulin and the fluid infusion device is an insulin infusion device.

5. An insulin fluid infusion device, comprising:
a housing having a first chamber and a second chamber, with a seal that separates the first chamber from the second chamber, and the seal defines an opening;
a fluid reservoir received within the second chamber of the housing that defines a reservoir chamber to receive a fluid, the fluid reservoir including a first end and a second end, the first end having an open perimeter and the second end terminates in a port that includes an outlet to define a fluid flow path, the fluid reservoir including a stopper disposed within the reservoir chamber and movable from the first end to the second end to dispense the fluid through the outlet, the stopper including at least one friction element that contacts an interior surface of the fluid reservoir, the fluid reservoir having a first pressure;
a reservoir cap coupled to the second end of the fluid reservoir that includes a connector needle received within the port downstream of a hydrophilic wicking membrane to define a fluid flow path from the fluid reservoir to a tubing coupled to an infusion unit, the tubing having a second pressure, the first pressure greater than the second pressure;
a drive system received within the first chamber of the housing having a slide, a motor, a gear box and a drive screw, at least the gear box and the drive screw surrounded by the slide, the motor drives the gear box to rotate the drive screw, the slide including a plurality of threads defined on an interior surface that threadably engage threads of the drive screw such that a rotation of the drive screw by the gear box translates the slide through the opening of the seal into the second chamber, the slide received within the reservoir chamber through the first end of the fluid reservoir, the slide translatable within the reservoir chamber, the slide having a projection received within a counterbore of the stopper and a shoulder that contacts the stopper to move the stopper from the first end to the second end to dispense the fluid through the outlet; and
the hydrophilic wicking membrane having a first surface in contact with the fluid and a second surface opposite the first surface, the second surface coupled to the interior surface of the second end of the fluid reservoir so as to be disposed entirely within the reservoir chamber, the hydrophilic wicking membrane coupled to the second end such that the at least one friction element is spaced apart from the wicking hydrophilic membrane when the stopper is moved to the second end, the wicking hydrophilic membrane completely covers the outlet to substantially prevent a flow of air into the fluid flow path and the difference between the first pressure and the second pressure cooperates with the hydrophilic wicking membrane to dispense the fluid through the outlet.

6. The fluid infusion device of claim 5, wherein the fluid is insulin.

7. The fluid infusion device of claim 5, wherein the hydrophilic wicking membrane is coupled to the second end of the fluid reservoir such that the hydrophilic wicking membrane is spaced apart from the slide of the drive system.

\* \* \* \* \*